GERANIUM PLANT
Filed Aug. 26, 1970 2 Sheets-Sheet 1
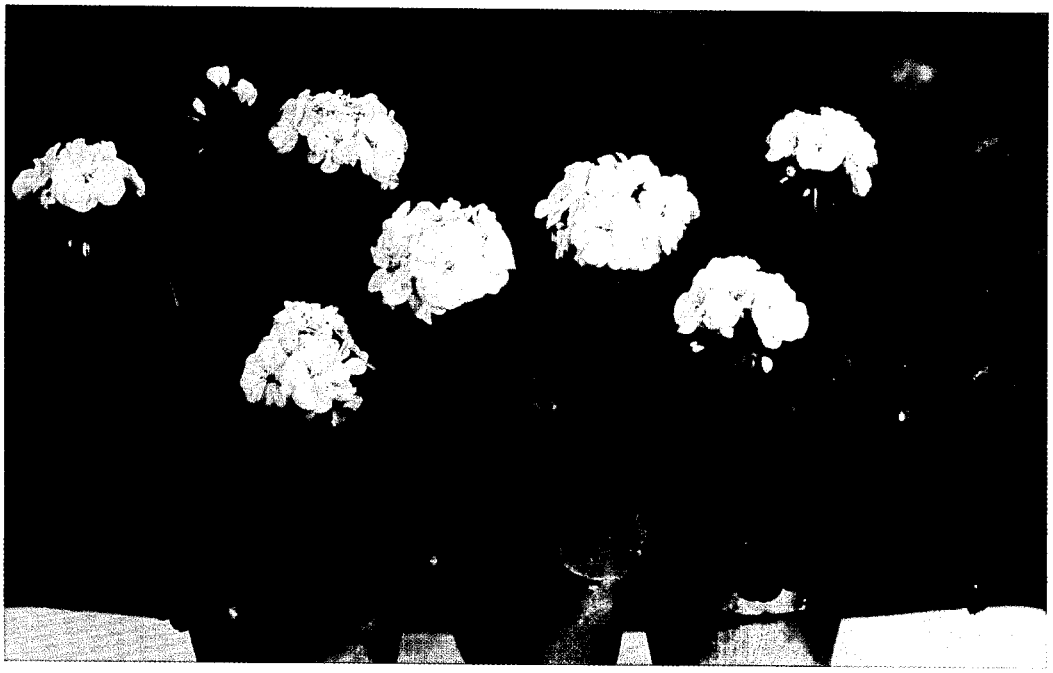

GERANIUM PLANT
Filed Aug. 26, 1970 2 Sheets-Sheet 2
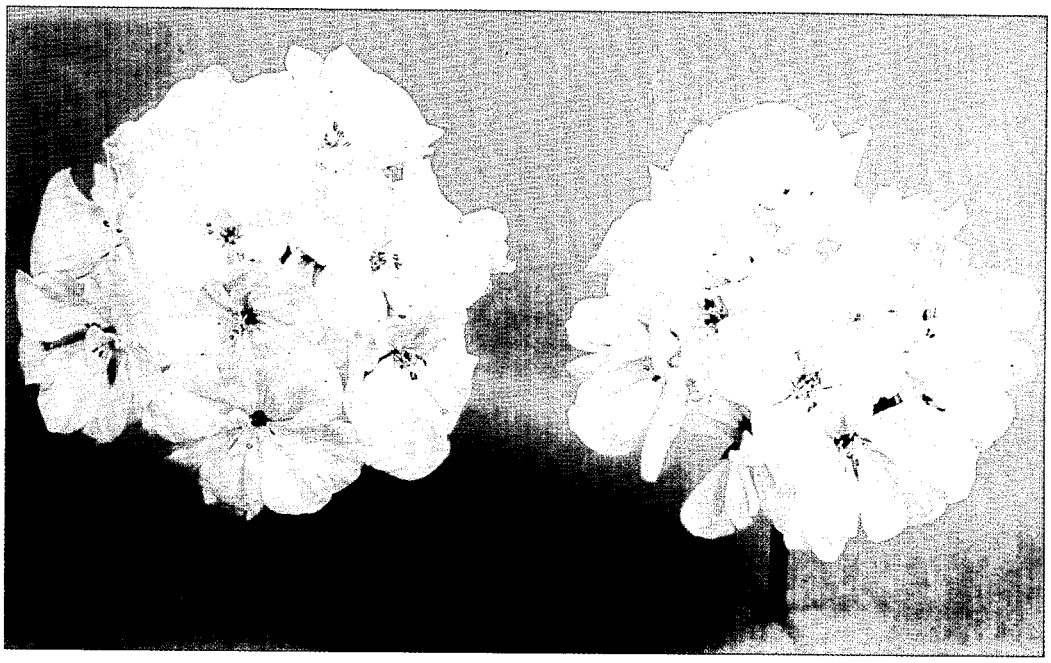

United States Patent Office

Plant Pat. 3,173
Patented May 16, 1972

3,173
GERANIUM PLANT

Walter W. Knicely, Barberton, and William E. Duffett, Akron, Ohio, assignor to Yoder Brothers, Inc., Barberton, Ohio Filed Aug. 26, 1970, Ser. No. 67,300
Int. Cl. A01h 5/00
U.S. Cl. Plt.—68 1 Claim The present invention comprises a new and distinct variety of geranium plant which has resulted from crossing certain geranium selections in a program of controlled hybridization. The seed parent is identified for breeding purposes as #423, and the pollen parent #6171–1, which numbers serve to distinguish these parents from others in the same breeding program.

The new variety is similar in many respects to the variety Snowball, an unpatented but commercial variety of Yoder Brothers, Inc., Barberton, Ohio, the assignee of the present invention. Both varieties have the same characteristics of:

(1) White semi-double flowers.

(2) Foliage of similar size and color.

The new variety is distinguished from Snowball by the following:

(1) Approximately 10 days earlier response than Snowball from a planting of 2″ potted plants to a saleable pot in a spring pot program.

(2) Foliage more resistant to botrytis than Snowball under outdoor conditions.

(3) Greater flower production than Snowball in Spring pots, averaging 1 to 2 more flowers per plant.

(4) In outdoor controlled plantings, Snowmass averages 2 to 3 more flowers per plant than Snowball.

(5) No tendency to "pink" with cooler temperatures in outdoor planting as does Snowball.

(6) Shows no tendency to become vegetative when watered heavily.

(7) Maintains a more compact habit than Snowball, which has a tendency to grow tall and leggy, especially in outdoor palntings.

The new variety is similar in many respects to the variety Summer Cloud, also an unpatented but commercial variety, having the same characteristics of:

(1) Semi-double white flowers.

(2) Similar flower production in spring pots.

The new variety is distinguished from Summer Cloud by the following:

(1) A purer white flower; does not "pink" in cooler outdoor conditions.

(2) It does not shatter.

(3) More resistant to botrytis in outdoor plantings.

(4) Has a lighter color foliage and a somewhat smaller leaf size.

(5) Has a more upright growth habit with less spreading tendencies in both spring pots and outdoor flowerings.

(6) Averages 2 to 3 more flowers per plant under outdoor conditions.

The new variety was selected from a progeny of seedlings from the above-mentioned parents. Varietal worth was determined by flowering cuttings taken from the inital selection in both a spring 4″ pot flowering program and in outdoor flowerings during the summer months.

My new variety has been asexually reproduced by cuttings at Barberton, Ohio, and has been found to maintain its distinctive characteristics through successive propagations.

My new variety when grown in a greenhouse in the vicinity of Barberton, Ohio, in a 4″ pot program has a response of 45 days. Geranium response is defined by Yoder Brothers, Inc., as the number of days from plant date of a 2″ potted plant in a 4″ pot to the date 80% of the pots in the test benches are saleable, when grown at a 65° night temperature. A saleable pot is a 4″ pot which has a minimum of 1 flower head showing color. It will be understood that the response time and blooming period may vary significantly with varying environmental conditions such as temperature, light intensity, and day length.

The accompanying drawings illustrates the new variety the colors being as nearly true as possible with color illustrations of this type. In the drawings, sheet 1 comprises a color photograph of the new cultivar by itself, and sheet 2 comprises a comparison color photograph, with the new cultivar appearing on the left and the cultivar Snowball on the right. Certain of the above mentioned characteristics which distinguish the new cultivar from the cultivar Snowball will be apparent from the comparison photograph.

The following detailed description is based on observations made both in the greenhouse and in outdoor plantings in the vicinity of Barberton, Ohio. Color references are made to the Munsell Color Book, 1963 edition. In the Snowball and Summer Cloud.

Botanical classification: Pelargonium × hortorum (Bailey)

*Flower*:

*Color.*—Spring color—White, N 9.5/—summer color—white, N 9.5/.

*Bud.*—Sheath—medium size, dissected, pubescant outside, smooth inside, persistent, tends to dry up as flower head matures; color, yellow-green 5GY6/8—calyx—five long, narrow, pointed, persistent; color, yellow-green, 5GY6/8.

*Inflorescense.*—Peduncle—strength, wiry, will support weight under rough handling; rather thin; somewhat hairy; length, 4″–8″; color, green, 5GY5/8—pedicel—medium to long, hairy; length, 1″–1½; color, green, 5GY5/8—petalage—semi-double, 8 to 12. Can have petaloid anthers and petaloid calyx—opening—opens well, florets flat when fully open; buds open in 2 days from tight bud.

*Lasting quality.*—Non-shatter; comeback following rain outdoors: excellent most durable of all whites to arin and sunburn.

*Reproductive organs.*—Stamen, anthers—5 to 10, may be petaloid—color—gray salmon-pink, 5R6/8—filaments—rather long, slender, white in color—pollen—orange, near 2.5YR5/12—pistil style—short, color quite pale green lighter than 2.5GY9/2—stigma—5-lobed, white, tips becoming rose 2.25R4/14 as plant ages—ovary—hypogynous, conoidal, hairy, light green, near 5GY6/6.

*Bloom habit.*—Response in spring 4″ pots to 80% saleability: Snowmass—45 days—Snowball—55 days—Summer Cloud—50 days.

Flower production: (flowers and buds per plant)

| | Spring | Summer |
|---|---|---|
| Snowmass | 3.5 | 8 |
| Snowball | 2 | 6 |
| Summer Cloud | 3.25 | 5 |

Spring production is defined by Yoder Brothers, Inc., as the average number of flowers and buds per 4″ pot visible above the foliage when 80% of the pots grown at 65° night temperature are saleable. Summer or outdoor production is defined by Yoder Brothers, Inc., as the average number of flowers and buds per plant visible above the foliage in early August from a June 1 planting of a 2″ potted plant.

*Continuity.*—Continuous.

Plant:

*Growth habit.*—4" spring pots, generally upright and less spreading than that of Summer Cloud. Similar to Snowball except more compact. Outdoors, plant maintains more compact growth than Snowball which grows tall and leggy; more upright and less spreading than Summer Cloud.

*Breaking action.*—Pinch not needed to develop well-branched plant.

*Stem.*—Medium caliber, nearly smooth, color light green, 5GY6%6.

*Stipule.*—Medium size, longer than wide, smooth green, 5GY5/6 stipules end to dry as plant matures.

*Foliage.*—Form—reinform—size—2" to 4"—margin — somewhat incised — texture — leathery—color — Snowmass — base color — green between 5.5GY5/8 and 5.5GY5/6—zonal markings—very slight, mainly a difference in intensity of green color—lower foliage—light gray-green between 7.5GY5/6 and 7.5GY5/4 — durability — foliage moderately resistant to botrytis—spray sensitivity—none.

*Rooting and stock production.*—Roots well in conventional geranium rooting period; growth rapid, produces cuttings well.

*Disease resistance.*—Foilage and flowers moderately resistant except in extremely wet and humid conditions.

I claim:

1. A new and distinct variety of geranium, characterized particularly by its early response and superior flower production in 4" pots in a spring pot program, superior flower production in an outdoor flowering program, a clear white color with no tendencies towards heavy watering conditions, and superior durability to outdoor conditions.

No references cited.

ROBERT E. BAGWILL, Primary Examiner

UNITED STATES PATENT OFFICE
CERTIFICATE OF CORRECTION

Patent No. PP 3,173 Dated May 16, 1972

Inventor(s) WALTER W. KNICELY and WILLIAM E. DUFFETT

It is certified that error appears in the above-identified patent and that said Letters Patent are hereby corrected as shown below:

In column 2, line 22, the sentence beginning in that line should read --In certain instances, comparisons have been made with the varieties Snowball and Summer Cloud.--

In column 3, line 11, "5GY6%6" should read --5GY6/6--.

In column 3, line 13, "end" should read --tend--.

In column 3, line 16, "reinform" should read --reniform--.

In claim 1, following line 5, the following should be inserted --pinking, superior reproductive flowering traits under--.

Signed and sealed this 22nd day of May 1973.

(SEAL)
Attest:

EDWARD M.FLETCHER,JR.
Attesting Officer

ROBERT GOTTSCHALK
Commissioner of Patents